(12) United States Patent
Deshpande et al.

(10) Patent No.: US 7,273,935 B2
(45) Date of Patent: Sep. 25, 2007

(54) PROCESS FOR THE PREPARATION OF 3-METHYLCEPHAM DERIVATIVES

(75) Inventors: Pandurang Balwant Deshpande, Chennai (IN); Udayampalayam Palanisamy Senthilkumar, Erode District (IN); Andrew Gnanaprakasam, Chennai (IN); Kanagaraj Sureshkumar, Tiruvarur (IN)

(73) Assignee: Orchid Chemicals & Pharmaceuticals, Ltd., Chennai (IN)

( * ) Notice: Subject to any disclaimer, the term of this patent is extended or adjusted under 35 U.S.C. 154(b) by 470 days.

(21) Appl. No.: 10/922,992

(22) Filed: Aug. 23, 2004

(65) Prior Publication Data
US 2005/0070705 A1  Mar. 31, 2005

(30) Foreign Application Priority Data
Aug. 21, 2003  (IN) .......................... 670/CHE/2003

(51) Int. Cl.
*C07D 501/08* (2006.01)
*C07D 499/063* (2006.01)

(52) U.S. Cl. ........................ 540/228; 540/230; 540/310
(58) Field of Classification Search ...................... None
See application file for complete search history.

(56) References Cited

U.S. PATENT DOCUMENTS 4,218,374 A * 8/1980 Kamiya et al. ............. 540/313

OTHER PUBLICATIONS

Tanaka, Bulletin of the Chemical Society of Japan 62 (1989), No. 9 pp. 3046-3048.*

* cited by examiner

*Primary Examiner*—Mark L. Berch
(74) *Attorney, Agent, or Firm*—Oliff & Berridge, PLC

(57) ABSTRACT

A process for the preparation of 3-methylcepham-4-carboxylate of the formula (I).

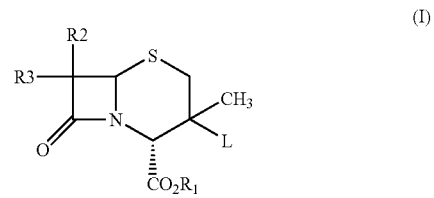

(I)

wherein $R^2$ and $R^3$ may be same or different and represent hydrogen, halogen, amino, alkyl, phenacetamido, substituted acetamido, phthalimido with a proviso that both $R^2$ and $R^3$ are not $NH_2$, phenacetamido, phthalimido and the like; $R_1$ represents a lower alkyl, p-methoxybenzyl, p-nitrobenzyl, o-nitrobenzyl, o-methoxybenzyl, o-chlorobenzyl or diphenylmethyl group, or a suitable ester residue which can be deprotected at a latter stage, L represents a leaving group; which comprises cyclizing the compound of formula (III)

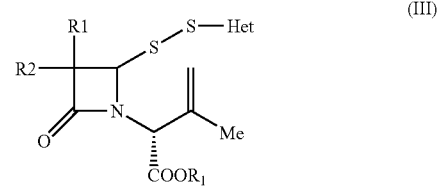

(III)

using a cyclizing agent in the presence of organic or inorganic nitrites and a solvent at a temperature in the range of −40° C. to +60° C. to obtain compound of formula (I).

6 Claims, No Drawings

PROCESS FOR THE PREPARATION OF 3-METHYLCEPHAM DERIVATIVES

FIELD OF THE INVENTION

The present invention relates to a process for the preparation of 3-methylcepham derivatives. More particularly, the present invention relates to a process for the preparation of 3-methylcepham-4-carboxylate of the formula (I).

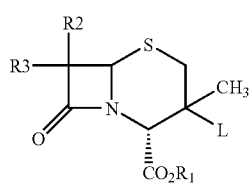

The 3-methylcepham-4-carboxylate of the formula (I) is a key intermediate in the preparation of 2β-substituted methyl-2α-methyl penicillin derivatives of the formula (II).

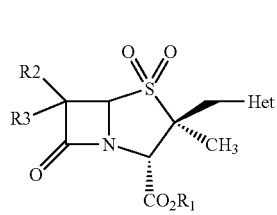

where $R^1$ represents hydrogen, carboxylic acid protecting group such as an ester or a pharmaceutically acceptable salt; $R^2$ and $R^3$ may be same or different and independently represent hydrogen, halogen, $NH_2$, phenacetamido, substituted acetamido, phthalimido with a proviso that both $R^2$ and $R^3$ are not $NH_2$, phenacetamido, phthalimido; Het represents a 5 or 6 membered —NH containing heterocyclic ring system containing one or more heteroatoms selected from O, S, or N.

BACKGROUND OF THE INVENTION

Several patents have disclosed various methods of producing 2β-substituted methyl-2α-methyl penicillin derivatives of the formula (II), but none of the patents disclosed the process using the intermediate of formula (I).

Tanaka et. al (Bull. Chem. Soc. Japan 62, 3046-3048 (1989)) describes a facile halogenative cyclization of 4-(2-benzothiazolyldithio)azetidinones and the susceptibility of 2-bromomethyl penams to isomerization to produce 3-bromocephams. The process reported that nitrosyl halide, generated from sodium nitrite and hydrogen halide in a biphasic water-dichloromethane medium, is shown to nitrosate the benzothiazolyl-nitrogen of the azetidinone derivative, thereby effecting the leaving of benzothiazolylthio group and forming the 2β-halomethylpenam.

The present invention is based on the mechanism that the protic acid itself directly reacts with the 4-(benzothiazolyldithio)azetidinone in a solvent to produce the cepham derivative, along with the by-product, 2-mercaptobenzothiazole. The 2-mercaptobenzothiazole was oxidized, by the addition of sodium nitrite, into 2,2'-dithiobis(benzothiazole), which is easier to remove from the reaction mixture owing to its less soluble nature and enable isolation of the cephem derivative.

OBJECTIVE OF THE INVENTION

The main objective of the present invention is to provide a process for the preparation of 3-methylcepham-4-carboxylate of the formula (I).

Yet another objective of the present invention is to develop a simple and commercially viable process for the preparation of 2β-substituted methyl-2α-methyl penicillin derivatives of the formula (II) using the compound of formula (I).

SUMMARY OF THE INVENTION

Accordingly, the present invention provides a process for the preparation of 3-methylcepham-4-carboxylate of the formula (I).

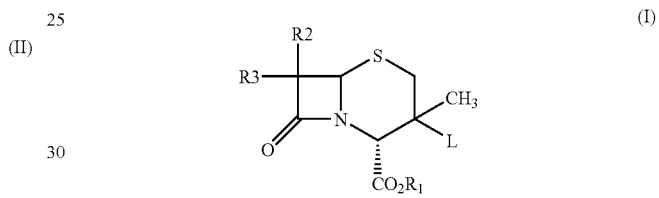

wherein $R^2$ and $R^3$ may be same or different and represent hydrogen, halogen, amino, alkyl, phenacetamido, substituted acetamido, phthalimido with a proviso that both $R^2$ and $R^3$ are not $NH_2$, phenacetamido, phthalimido and the like; $R^1$ represents a lower alkyl, p-methoxybenzyl, p-nitrobenzyl, o-nitrobenzyl, o-methoxybenzyl, o-chlorobenzyl or diphenylmethyl group, or a suitable ester residue which can be deprotected at a latter stage, L represents a leaving group such as halogen like chloro, bromo, or iodo, tosylate, mesylate, triflate and the like, which comprises the steps of:

cyclizing the compound of formula (III)

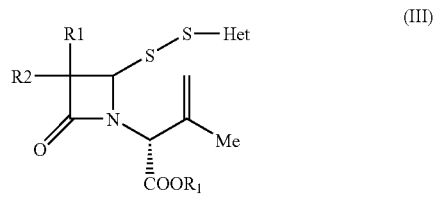

using a cyclizing agent in the presence of organic or inorganic nitrites and a solvent at a temperature in the range of −40° C. to +60° C. to obtain compound of formula (I).

DETAILED DESCRIPTION OF THE INVENTION

In an embodiment of the present invention organic or inorganic nitrites used is selected from sodium nitrite, potassium nitrite, or organic nitrites such as amyl nitrite, isoamyl nitrite, nitrosonium tetrafluoroborate, and the like; and the cyclizing agent used is selected from acids such as HCl, HBr, p-toluenesulfonic acid, methanesulfonic acid; and/or halogenating agents such as bromine, chlorine, IBr, BrCl and the like or mixture thereof.

In an embodiment of the present invention, the solvent used is selected from DMF, acetonitrile, N,N-dimethylacetamide, ethyl acetate, N-methyl-2-pyrrolidin-2-one, dioxane, THF, methylene dichloride, diethyleneglycol dimethyl ether, ethylene dichloride, toluene and the like. The reaction is carried out at a temperature in the range of −30° C. to +60° C.

In another embodiment of the present invention, the purpose of using nitrite is to eliminate the mercaptobenzothiazole formed in the reaction and it does not have any role in the reaction per se. The elimination of mercaptobenzo thiazole is necessary in order to avoid the formation of impurities in the final product.

In yet another embodiment of the present invention, the compound of formula (I) is a useful intermediate in the preparation 2β-substituted methyl-2α-methyl penicillin derivatives of the formula (II)

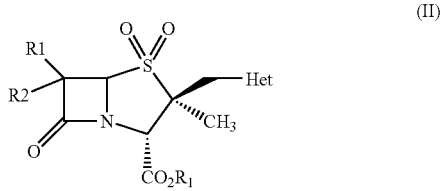

(II)

where $R^1$ represents hydrogen, carboxylic acid protecting group such as an ester or a pharmaceutically acceptable salt; $R^2$ and $R^3$ may be same or different and independently represent hydrogen, halogen, $NH_2$, phenacetamido, phthalimido with a proviso that both $R^2$ and $R^3$ are not $NH_2$, phenacetamido, phthalimido; Het represents a 5 or 6 membered NH containing heterocycle ring system containing one or more heteroatoms selected from O, S, or N.

In yet another embodiment of the present invention, the compound of formula (I) can be converted into tazobactam of formula (II)

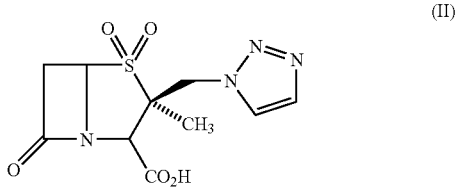

(II)

from the method given in our copendig application Ser. No. 10/309,201

In still another embodiment of the present invention the starting material p-Nitrobenzyl 2-oxo-4-(benzothiazol-2-yl)dithio-α-isopropenyl-1-azetidine acetate is prepared from the method available in the prior art.

The following examples are provided by way of illustration only and should not be limited to construe the scope of the invention.

EXAMPLE 1

Preparation of
p-nitrobenzyl-3-bromo-3-methylcepham-4-carboxylate p-Nitrobenzyl 2-oxo-4-(benzothiazol-2-yl)dithio-α-isopropenyl-1-azetidine acetate (200 g) was added to N,N-dimethylformamide (1000 mL) at 25-30° C. under stirring. To the clear solution obtained, hydrobromic acid (48% w/w, 150 mL) was added over a period of 40 min at 25-30° C. and stirred for 30 min. A solution of sodium nitrite (27.5 g in 120 mL water) was added over 30 min and stirring continued for 120 min. After the reaction was over, the reaction mixture was filtered and sucked well. The filtrate was charged slowly into a stirred mixture of ethyl acetate and water over a period of 30 min at 0-5° C. The pH was set to 5.0-5.5 with sodium bicarbonate solution and the aqueous layer extracted with ethyl acetate three times. The organic layers were combined, washed with water, and charcoalized. The solvent was distilled off under vacuum until a thick slurry was obtained. Ethyl acetate and diisopropyl ether were added, stirred well at 25-30° C., filtered, and washed with ethyl acetate-diisopropyl ether mixture. Drying under vacuum for 6-8 hrs at 25-30° C. afforded the pure title compound (107-125 g).

EXAMPLE 2

Preparation of
p-nitrobenzyl-3-bromo-3-methylcepham-4-carboxylate p-Nitrobenzyl 2-oxo-4-(benzothiazol-2-yl)dithio-α-isopropenyl-1-azetidine acetate (200 g) was added to N,N-dimethylformamide (1000 mL) at 25-30° C. under stirring. To the clear solution obtained, hydrobromic acid (48% w/w, 150 mL) was added over a period of 40 min at 25-30° C. A solution of sodium nitrite (27.5 g in 120 mL water) was added over 40 min and stirring continued for 120 min. After completion of the reaction, the reaction mixture was cooled to 0-5° C. and sodium bicarbonate added until pH was in the range 4.0-4.5. The reaction mixture was cooled to −5° C., water (550 mL) added under stirring and filtered. The wet cake was charged into ethyl acetate (1000 mL), stirred well and filtered. The filtrate was washed with water twice and charcoalized. Solvent was distilled off under vacuum until thick slurry was obtained. Ethyl acetate and diisopropyl ether were added, stirred well at 25-30° C., filtered, and washed with ethyl acetate-diisopropyl ether mixture. Drying under vacuum for 6-8 hrs at 25-30° C. afforded the pure title compound (110-130 g).

EXAMPLE 3

Preparation of
p-nitrobenzyl-3-bromo-3-methylcepham-4-carboxylate p-Nitrobenzyl 2-oxo-4-(benzothiazol-2-yl)dithio-α-isopropenyl-1-azetidine acetate (200 g) was added to N,N-dimethylformamide (1000 mL) at 25-30° C. under stirring. To the clear solution obtained, hydrobromic acid (48% w/w, 150 mL) was added over a period of 40 min at 25-30° C. A solution of sodium nitrite (27.5 g in 120 mL water) was added over 40 min and stirring continued for 120 min. After completion of the reaction, the reaction mixture was cooled to 0-5° C. and sodium bicarbonate added until pH was in the range 4.0-4.5. The reaction mixture was cooled to −5° C., water (550 mL) added under stirring and filtered. The wet cake was charged into ethyl acetate (1000 mL), stirred well and filtered. The filtrate was washed with water twice and charcoalized. The solvent was distilled off under vacuum until a thick slurry was obtained. Diethyl ether was added, stirred well at 25-30° C., filtered, and dried under vacuum for 30 min to afford pure title compound (110-130 g).

We claim:

1. A process for the preparation of 3-methylcepham-4-carboxylate of the formula (I)

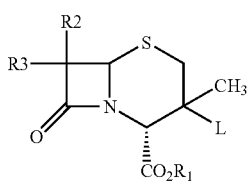

(I)

wherein $R^2$ and $R^3$ may be same or different and represent hydrogen, halogen, amino, alkyl, phenacetamido, substituted acetamido, phthalimido with a proviso that $R^2$ and $R^3$ are not both $NH_2$, phenacetamido or phthalimido; $R_1$ represents a lower alkyl, p-methoxybenzyl, p-nitrobenzyl, o-nitrobenzyl, o-methoxybenzyl, o-chlorobenzyl or diphenylmethyl group, L represents a leaving group selected from the group consisting of chloro, bromo, iodo, tosylate, mesylate and triflate; which process comprises cyclizing the compound of formula (III)

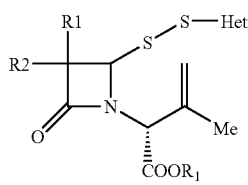

(III)

wherein Het represents a 5 or 6 membered—N— containing heterocyclic ring, which contains one or more heteroatoms selected from O, S and N, with a cyclizing agent, which introduces the leaving group L, in a polar organic solvent at a temperature in a range of −40° C. to 60° C., adding a solution of organic or inorganic nitrites, and isolating the compound of formula (I) without utilizing chromatographic techniques.

2. The process according to claim 1, wherein the cyclizing agent is selected from HCl, HBr, p-toluenesulfonic acid, methanesulfonic acid, bromine, chlorine, IBr, BrCl, and mixtures thereof.

3. The process according to claim 1, wherein the organic or inorganic nitrites is selected from sodium nitrite, potassium nitrite, amyl nitrite, and isoamyl nitrite.

4. The process according to claim 1, wherein the solvent is selected from N,N-dimethylformamide, acetonitrile, N,N-dimethylacetamide, N-methyl-2-pyrrolidin-2-one, dioxane, and mixtures thereof.

5. The process according to claim 1, further comprising converting the compound of formula (I) in to 2β-substituted methyl-2α-methyl penicillin derivatives of the formula (II)

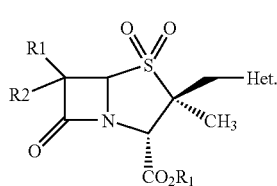

(II)

6. The process according to claim 5, wherein the 2β-substituted methyl-2α-methyl penicillin derivatives of the formula (II) is Tazobactam.

\* \* \* \* \*